United States Patent [19]

Can

[11] Patent Number: 5,422,711
[45] Date of Patent: Jun. 6, 1995

[54] GEM VIEWING AND MANIPULATION APPARATUS

[76] Inventor: Hanna Can, 15036 Tyacke Dr., Burnsville, Minn. 55337

[21] Appl. No.: 138,355

[22] Filed: Oct. 18, 1993

[51] Int. Cl.⁶ .............................................. G01N 21/87
[52] U.S. Cl. ............................................................ 356/30
[58] Field of Search ..................... 348/86, 92, 125, 128, 348/135; 356/30

[56] References Cited

U.S. PATENT DOCUMENTS

| | | | |
|---|---|---|---|
| 1,700,496 | 1/1929 | Heitzler | 356/30 |
| 1,700,497 | 1/1929 | Heitzler | 356/30 |
| 2,742,813 | 4/1956 | Zeininger | 356/30 |

FOREIGN PATENT DOCUMENTS

| | | | |
|---|---|---|---|
| 3914882 | 11/1990 | Germany | 356/30 |
| 120939 | 9/1981 | Japan | 356/30 |
| 200210 | 11/1983 | Japan | 356/30 |

*Primary Examiner*—F. L. Evans
*Attorney, Agent, or Firm*—Palmatier, Sjoquist & Helget

[57] ABSTRACT

The present invention provides an improved apparatus for viewing gems that provides a magnified image simultaneously viewable by several individuals, and which allows a customer to manipulate the gem while restricting the customer's access to the gem and without any physical contact with the gem by the customer. The apparatus is comprised of a horizontal base with two opposing panels. A television camera with a magnifying lens extends from one upright panel to provide a viewing region immediately above a receiving placement zone on the base. A light source is provided adjacent to the camera on the same upright panel. A background screen is located on the opposing upright panel. A pair of opposing elongate fingers are pivotally and slidably mounted on a post that extends from the horizontal base adjacent the placement zone. The opposing jaws are configured to grasp a gem placed in the placement zone, raise the gem to the viewing region, and manipulate the gem in the viewing region as desired for viewing of the gem. A television monitor displays the image. The device is particularly applicable in the retail sales of jewelry.

19 Claims, 1 Drawing Sheet

GEM VIEWING AND MANIPULATION APPARATUS

BACKGROUND OF THE INVENTION

This invention relates to an apparatus for viewing objects, more specifically, it relates to apparatus to allow the viewing of the magnified image of gems on a television monitor while simultaneously manipulating the gems.

The equipment conventionally used for magnifying and viewing gems are the eyepiece, commonly known as the loupe, and the microscope. Both the loupe and microscope can be difficult to use, especially for lay people, and are cumbersome for use during sales presentations. A principal disadvantage is that only one person can view the image of the gem through either of these apparatus at any one time. This is particularly disadvantageous when a jeweler or gemologist is attempting to point out specific features or flaws in a particular gem. An additional disadvantage is that the loupe requires the viewer to hold or come into close contact with the gem being viewed. Additionally, with conventional viewing equipment the jeweler or gemologist may loose visual contact with the gem during handling by the customer, presenting security problems.

SUMMARY OF THE INVENTION

The present invention provides an improved apparatus for viewing gems that provides a magnified image simultaneously viewable by several individuals, and which allows a customer to manipulate the gem while restricting the customer's access to the gem and without any physical contact with the gem by the customer. The apparatus is comprised of a horizontal base with two opposing panels. A television camera with a magnifying lens extends from one upright panel to provide a viewing region immediately above a receiving placement zone on the base. A light source is provided adjacent to the camera on the same upright panel. A background screen is located on the opposing upright panel. A pair of opposing elongate fingers are pivotally and slidably mounted on a post that extends from the horizontal base adjacent the placement zone. The opposing jaws are configured to grasp a gem placed in the placement zone, raise the gem to the viewing region, and manipulate the gem in the viewing region as desired for viewing of the gem. A television monitor displays the image. The device is particularly applicable in the retail sales of jewelry.

A feature of the present invention is that it permits several individuals to simultaneously view the same image of a gem. This allows specific features of the gem to be pointed out by referencing the features on the image shown on the television monitor.

An additional advantage of the invention is that the actual gem and the magnified image of the gem can both be viewed simultaneously.

Another advantage and feature of the invention is that physical access by customers to gems placed on the receiving tray or in the elongate fingers is restricted, while still allowing the customer to view the magnified image of a gem and to manipulate the gem.

A significant feature of the invention is that it allows an individual, such as a customer, to view a magnified image of a gem while manipulating the gem, and eliminates or minimizes the need for the physical handling of the gem. This provides security and helps to keep the gem clean.

Another advantage of the present invention is that by focusing through the gem imperfections or flaws may be more easily identified and viewed, especially by lay people.

Another feature of the present invention is that a convenient side by side magnified viewing of two or more gems may be performed permitting direct comparisons between gems. Additionally, gems may be viewed with color comparison charts.

An additional feature of the invention is that a magnified video image of the gem may be conveniently recorded by way of conventional video recording apparatus.

DETAILED DESCRIPTION OF THE PREFERRED EMBODIMENTS

The apparatus as depicted is intended principally for use by those in the jewelry business, especially the retail sale of jewelry although other uses will become apparent. "Gems" as used herein is intended to encompass all stones, jewelry, watches, or other items which may be viewed in the apparatus.

Figure 1:
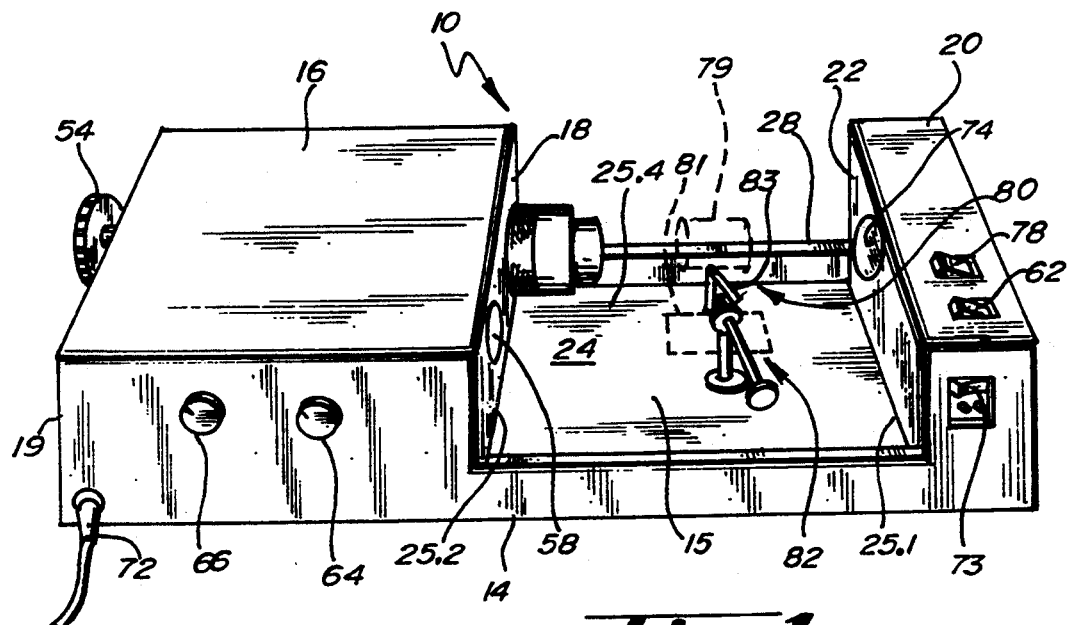
FIG. 1 is a perspective of the invention.
Figure 2:
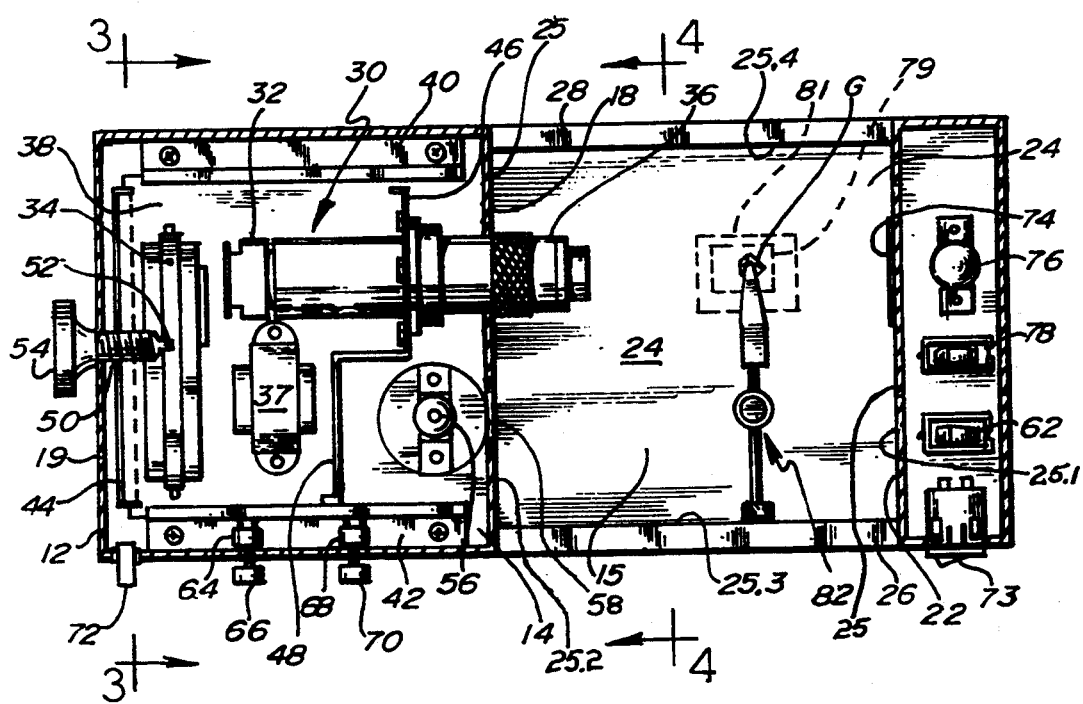
FIG. 2 shows a plan view with the first enclosure and second enclosure removed, showing the general layout of the components.

Referring to FIGS. 1 and 2, the viewing and manipulation apparatus is shown and is indicated by the numeral 10, with a gem indicated by letter G. FIG. 1 shows the apparatus with enclosures in place. In FIG. 2 portions of the enclosures are removed to show the general layout of components. Wiring is not shown. The apparatus 10 is generally comprised of a horizontal base 14 having an upper surface 15, a first enclosure 16 including a first upright panel 18 and a back panel 19, and a second enclosure 20 with a second upright panel 22 opposite the first upright panel 18. Intermediate the two upright panels 18, 22 on the horizontal base 14 is a receiving region 24. The receiving region 24 has an outer perimeter 25, a first end 25.1; a second end 25.2, a first side 25.3, and a second side 25.4. Two raised edges 26, 28 extend between the two upright panels 18, 22 along the first side 25.3 and the second side 25.4 respectively. Included within the first enclosure 16 is a television camera means 30 which comprises the components of a television camera and principally includes a solid state sensor 32, a circuit board 34, and a lens 36 extending out the first upright panel 18. The lens 36 is directed horizontally toward the second upright panel 22. A transformer 37 provides power for the camera 30. The camera lens 36, the sensor 32, the circuit board 34, and the transformer 37 are all mounted by screws, rivets or other suitable means to a sliding chassis 38. The sliding chassis 38 is supported by and rides in guides 40, 42 which are attached to the base 14. The sliding chassis 38 is formed of a rigid material such as sheet metal. The guides 40, 42 may be suitably formed of machined aluminum or plastic.

Figure 3:
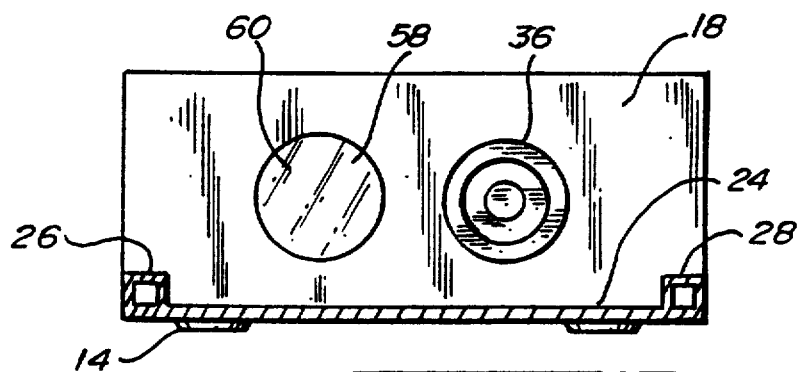
FIG. 3 is a sectional taken at line 3—3 of FIG. 2 and shows the sliding chassis.

Referring to FIGS. 2 and 3, the sliding chassis 38 has a first vertical wall 44, a second vertical wall 46, and a third vertical wall 48. The camera lens 36 and solid state sensor 32 are mounted on the second vertical wall 46. Suitably attached to the first vertical wall 44 is drive nut 50. A threaded shaft 52 is engaged within the drive nut 50 and extends through and is rotatably mounted to the back panel 19. A knob 54 is attached to the shaft. Rotation of the knob 54 adjustably slides the chassis 12 forwardly and rearwardly with respect to the back panel 22.

Figure 4:
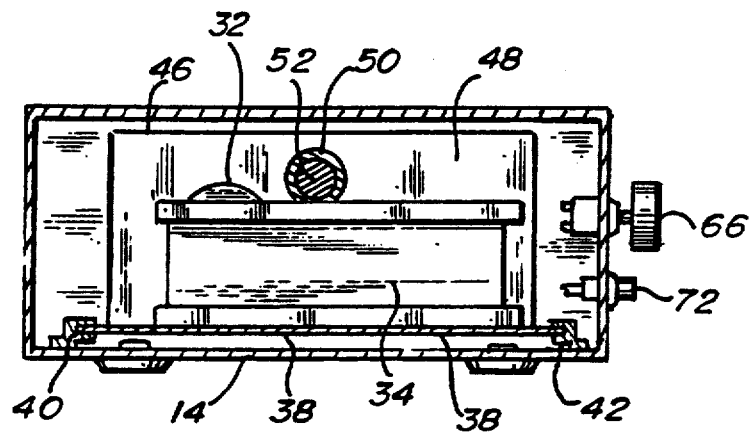
FIG. 4 is a sectional taken at line 4—4 of FIG. 2.

Located behind the first panel 18 is a first light source 56 which may provide illumination of the gem at an oblique angle relative to the camera through an aperture 58 which is best shown in FIG. 4. A lens or diffuser 60 is attached to the first upright panel 18 and covers the aperture 58. A rocker switch 62 mounted on the second enclosure controls the first light source 56. The first light source 56 may also be adjustable relative to its intensity by conventional means. Also extending out of the first enclosure is a color control 64 with a knob 66, an iris control 68 with a knob 70, and a video output jack 72. A combination power switch and power cord receptacle 73 is shown connected to the second enclosure 20.

As best seen in FIG. 1, attached to the second upright panel 22 is a background screen 74 which provides the background when viewing the gem G. The screen 74 may be back lit by way of a second light source 76 within the second enclosure 20, best shown in FIG. 2. The background screen 74 may be interchangeable with alternate screens having different colors, shades and/or different degrees of translucency. A rocker switch 78 controls the second light source 76. The second light source 76 also may be adjustable by conventional means with regard to its intensity.

The television camera means 30 is a conventional television camera with the components of the camera mounted on the sliding chassis 38 and contained within the first enclosure 16. A suitable camera would be a model VCM7250 by Philips Consumer Electronics B.V. An appropriate lens would be a microscope lens with a variable zoom of 0.75× to 3× power and a working distance of 61 mm. The working distance of the lens 36 defines a viewing region 79 indicated by phantom lines above the base 14 and intermediate the first and second upright panels 18, 22. The gem is positioned and manipulated within the viewing region 79. Immediately below the viewing region 79 is the placement zone 81 positioned on the base 14.

Figure 5:
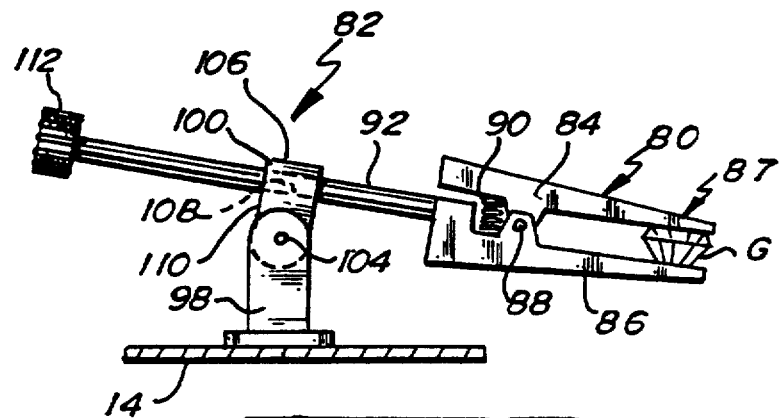
FIG. 5 is a detail figure of the grasping means and manipulation means of the invention.

The grasping means 80 and the manipulation means 82 are shown in FIGS. 1, 2 and 5. Referring to FIG. 5, the grasping means 80 is comprised of a clip 83 formed of elongate fingers 84, 86 having a grasping portion 87 and pivotally connected at a pin 88, a spring 90 is inserted between the elongate fingers 84, 86 to provide a bias.

The manipulation means 82 is comprised principally of a post 98, a post extension 100, a pin 104, an upper portion 106, a hole 108, and a lower portion 110. The post 98 is suitably attached to the base 14 by way of a screws, adhesives, or other appropriate means. The post extension 100 is pivotally attached to the post 98 by a pin 104. The post extension 100 has an upper portion 106 which includes a hole 108 and a lower portion 110 to which the upper portion 106 is rotatably attached by suitable means. The rod 92 is connected to one of the elongate fingers 84, 86 and extends through a pivoting post hole 108 in the post extension 100. A knurled knob 112 is attached to the end of the rod 92. The hole 108 is sized to allow the rod 92 to be rotatably and slidably adjusted therein.

The sizing and configuration of the component parts of the grasping means 80 and manipulation means 82 allows the grasping of gems placed on the receiving region 24 immediately below the viewing region 79 in an area shown as the placement zone 81. Gems grasped by the grasping means 80 in the placement zone 81 may be elevated into and manipulated within the viewing region 79. Alternate manipulation means may also be utilized such as a flexible post which retains a deformation. The function of the manipulation means is to be able to adjust the position of the gem and have the gem G be retained in the adjusted position.

Alternate grasping means would include adhesive or suction elements to grasp the gem G. The function of the grasping means is to clamp or attach to the gem while leaving substantially all of the gem G exposed for viewing. Additionally, more than one grasping means and manipulation means can be utilized with said means mounted above, adjacent to, or opposite the placement of the grasping means 80 and manipulation means 82 as shown. This would allow comparative viewing of multiple gems and also may be utilized for viewing a gem in conjunction with a reference chart.

The apparatus is utilized as follows: Referring to FIGS. 1 and 2, a display means such as a television monitor, not shown, is connected to the apparatus by conventional means through the video output jack 72. The rocker switches 62, 78 are turned on as desired to control the first light source 56 and the second light source 66. A gem G is placed within the elongate fingers 84, 86 or is placed in the placement zone 81 and is then grasped by the elongate fingers 84, 86. The gem G engaged by the elongate fingers 84, 86 is manipulated by utilizing the pivoting, sliding, and rotational characteristics of the rod 92, the post 98, and the post extension 100, and is positioned within the viewing range as desired. Appropriate magnification of the lens is selected and the lens 36 is focused by rotation of knob 54 which minutely slides the sliding chassis 38 containing the camera lens 36 and other camera components. The color control 64 and iris control 68 may be adjusted by way of knobs 66, 70. With an expanded iris a shorter field of view is given and the focus may be taken directly through the gem by adjusting the focus knob 54 to easily identify flaws and imperfections in the gem. A restricted iris gives a longer field of view and permits the gem to be rotated or otherwise repositioned in the viewing region 79 while still maintaining the gem in focus.

When utilized in jewelry sales presentations, the customer can adjust the focus by way of the knob 54 and can manipulate the gem G being viewed without any actual touching of the gem G by the customer. The arrangement of the first enclosure 16, the second enclosure 20, and the grasping means and manipulation means effectively discourages and restricts access to the viewing region 79 and the placement zone 81 and gems placed therein by customers. Any reaching into the viewing region 79 or the placement zone 81 by the customer is awkward and obvious. While the gem G is being manipulated the jeweler can easily point out specific features on the image shown on the television monitor.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A viewing and articulation apparatus for gems, the apparatus comprising:
   a) a horizontal and substantially planar support base having a first end, a second end, a receiving region intermediate the first and second ends, and an upper surface;
   b) a first enclosure mounted on the support base at the first end, the first enclosure having a first upright panel adjacent to and normal to the receiving region, the first upright panel having an aperture;
   c) a second enclosure mounted on the support base at the second end; the second enclosure having a second upright panel, the second upright panel adjacent to and normal to the receiving region and opposite the first upright panel, whereby the first and second enclosures restrict horizontal access to the receiving region;
   d) a television camera means within the first enclosure, the television camera means including a lens extending through the aperture in the first upright panel; the lens directed toward the second upright panel and having a viewing region intermediate the lens and the second upright panel;
   e) a grasping means for grasping a gem; and
   f) a manipulation means connected to the grasping means for manipulating the gem, the manipulation means extending upwardly from the support base whereby the manipulation means and the grasping means are positioned above the receiving region and whereby the grasping means is movable within the viewing region.

2. The apparatus of claim 1 further comprising a chassis slidably mounted to the support base within the first enclosure, a drive nut attached to the chassis, a threaded shaft rotatably connected to and extending through the first enclosure, the threaded shaft engaged with the drive nut, and wherein the lens is mounted to the chassis, whereby rotation of the threaded shaft slides the chassis and lens forwardly and backwardly.

3. The apparatus of claim 1, wherein the grasping and manipulation means comprises a post extending from the base and an elongate clip with a grasping portion for grasping the gems, the clip pivotally and rotatably mounted on the post, the post extending from the base and positioned so that the grasping portion extends into the viewing region.

4. The apparatus of claim 3, wherein the clip comprises outwardly extending opposing jaws pivotally connected, the jaws biased together for gripping the gems.

5. The apparatus of claim 1 further comprising a light source mounted to the base, the light source positioned to direct light at an oblique angle towards the viewing region with respect to the television camera.

6. The apparatus of claim 3, wherein the base and clip are configured whereby the grasping portion of the clip is movable between the surface of the receiving region and the viewing region.

7. The apparatus of claim 1 further comprised of a background screen attached to the second enclosure, the background screen positioned opposite the camera with respect to the viewing region.

8. The apparatus of claim 7, wherein the background screen is translucent and the apparatus further comprises a light source adjacent the background screen in the second enclosure.

9. The apparatus of claim 1, wherein the second enclosure is comprised of a translucent background screen and the apparatus further comprises a light source adjacent the background screen inside the second enclosure.

10. A viewing and manipulation apparatus for gems, the apparatus comprising:
   a) a horizontal support base with an upper surface;
   b) a television camera mounted to the support base, the television camera having a viewing region in front of the camera, the camera positioned to place the viewing region above and adjacent to the support base;
   c) a placement zone on the upper surface of the horizontal base positioned below the viewing region; and
   d) a pair of opposing elongate fingers pivotally connected to each other and having a closing bias for gripping gems, a post attached to the base, the fingers pivotally and rotatably attached to the post, the fingers and post configured to permit grasping a gem placed in the placement zone and manipulation of the gem into the viewing region.

11. The apparatus of claim 10 further comprising a background screen attached to the base and facing the television camera, the background screen positioned opposite the viewing region with respect to the camera.

12. The apparatus of claim 11, further comprising a light source mounted to the base, the light source positioned to direct light at an oblique angle towards the viewing region with respect to the television camera.

13. The apparatus of claim 12, wherein the light source has an intensity which is adjustable.

14. The apparatus of claim 11, wherein the background screen is comprised of a translucent background screen and the apparatus further comprises a light source adjacent the background screen.

15. The apparatus of claim 14, wherein the background screen is interchangeable.

16. The apparatus of claim 10, wherein the base has a perimeter surrounding the placement zone, a first side, a second side, a first end and a second end, the sides and ends positioned at the perimeter, the apparatus further comprising a first upright panel and a second upright panel positioned on the base at the first end and second end respectively, whereby horizontal access to the placement zone is restricted at the first end and the second end.

17. A viewing and manipulation apparatus for gems, the apparatus comprising:
   a) a horizontal and substantially planar support base having a first end, a second end, a receiving region intermediate the first and second ends, and an upper surface;
   b) a first enclosure mounted on the support base at the first end, the first enclosure having a first upright panel adjacent to and normal to the receiving region, the first upright panel having an aperture;
   c) a second enclosure mounted on the support base at the second end; the second enclosure having a second upright panel, the second upright panel adjacent to and normal to the receiving region and opposite the first upright panel, whereby the first and second enclosures restrict horizontal access to the receiving region;

d) a television camera means within the first enclosure, the television camera means including a lens extending through the aperture in the first upright panel; the lens directed toward the second upright panel and having a viewing region intermediate the lens and the second upright panel; and e) a pair of opposing elongate fingers pivotally connected to each other and having a closing bias for gripping gems, a post attached to the base the fingers pivotally and rotatably attached to the post, the fingers and post configured to permit grasping a gem placed in the receiving region and manipulation of the gem into the viewing region.

18. The apparatus of claim 17 further comprising a chassis slidably mounted to the support base within the first enclosure, a drive nut attached to the chassis, a threaded shaft rotatably connected to and extending through the first enclosure, the threaded shaft engaged with the drive nut, and wherein the lens is mounted to the chassis, whereby rotation of the threaded shaft slides the chassis and lens forwardly and backwardly.

19. The apparatus of claim 17 further comprising a light source mounted to the base, the light source positioned to direct light at an oblique angle towards the viewing region with respect to the television camera.

* * * * *

UNITED STATES PATENT AND TRADEMARK OFFICE
CERTIFICATE OF CORRECTION

PATENT : 5,422,711

DATED : June 6, 1995

INVENTOR(S) : Hanna Can

It is certified that error appears in the above-identified patent and that said Letters Patent is hereby corrected as shown below:

In the Drawings:

Add the attached Drawing Sheet, consisting of Figs. 3, 4, and 5.

Signed and Sealed this

Nineteenth Day of September, 1995

*Attest:*

BRUCE LEHMAN

*Attesting Officer*     *Commissioner of Patents and Trademarks*